United States Patent
Van Der Pol

(10) Patent No.: US 12,213,705 B2
(45) Date of Patent: Feb. 4, 2025

(54) SPINAL COLUMN IMPLANT CONNECTION DEVICE

(71) Applicant: SIGNUS MEDIZINTECHNIK GMBH, Alzenau (DE)

(72) Inventor: Bas Van Der Pol, Alzenau (DE)

(73) Assignee: SIGNUS MEDIZINTECHNIK GMBH, Alzenau (DE)

( * ) Notice: Subject to any disclaimer, the term of this patent is extended or adjusted under 35 U.S.C. 154(b) by 423 days.

(21) Appl. No.: 17/627,369

(22) PCT Filed: Jul. 30, 2020

(86) PCT No.: PCT/EP2020/071578
§ 371 (c)(1),
(2) Date: Jan. 14, 2022

(87) PCT Pub. No.: WO2021/019046
PCT Pub. Date: Feb. 4, 2021

(65) Prior Publication Data
US 2022/0257286 A1    Aug. 18, 2022

(30) Foreign Application Priority Data

Jul. 30, 2019   (DE) ..................... 10 2019 005 374.5

(51) Int. Cl.
*A61B 17/70*    (2006.01)
*A61B 17/00*    (2006.01)

(52) U.S. Cl.
CPC .. *A61B 17/705* (2013.01); *A61B 2017/00477* (2013.01)

(58) Field of Classification Search
CPC ............ A61B 17/705049; A61B 17/70; A61B 17/7001; A61B 17/68; A61B 17/7007; A61B 17/705
See application file for complete search history.

(56) References Cited

U.S. PATENT DOCUMENTS 10,206,718 B1 *  2/2019  Di Lauro ............ A61B 17/8665
10,278,735 B2 *  5/2019  Abell .................. A61B 17/7089
(Continued)

FOREIGN PATENT DOCUMENTS

DE    102011113235 A1    3/2013
EP       2581057 B1      8/2017
(Continued)

OTHER PUBLICATIONS

English Translation of International Preliminary Report on Patentability Dated Feb. 1, 2022, 8 Pages.

Primary Examiner — Ellen C Hammond
Assistant Examiner — Holly Joanna Lane
(74) Attorney, Agent, or Firm — LUCAS & MERCANTI, LLP; Klaus P. Stoffel

(57) ABSTRACT

A connection device for connecting an end region of an already implanted first spinal column support, at which pedicle screws are coupled on their head side to a first connection rod by respective coupling devices, to an already or not yet implanted spinal column support portion having a pedicle screw and extending the first spinal column support, having a first fastening arrangement for fastening the connection device to the first connection rod and a coupling for the extending support portion, in particular a second rod to be coupled to the pedicle screw of the extending support portion or a second fastening arrangement for fastening the connection device to such a second rod, further having a rigid bridge, laterally clinging to the coupling device of the closest pedicle screw of the first spinal column support on the connection side, of an intermediate region between the first fastening arrangement and the coupling.

19 Claims, 6 Drawing Sheets

(56) References Cited

U.S. PATENT DOCUMENTS

| | | | |
|---|---|---|---|
| 11,020,152 B2* | 6/2021 | Keyer | A61B 17/7034 |
| 2005/0234451 A1* | 10/2005 | Markworth | A61B 17/7005 |
| | | | 606/301 |
| 2008/0234743 A1 | 9/2008 | Marik | |
| 2009/0177232 A1 | 7/2009 | Kiester | |
| 2010/0217334 A1* | 8/2010 | Hawkes | A61B 17/7007 |
| | | | 29/446 |
| 2012/0253397 A1* | 10/2012 | Kraus | A61B 17/7049 |
| | | | 606/250 |
| 2013/0018421 A1* | 1/2013 | George | A61B 17/88 |
| | | | 29/428 |
| 2017/0348026 A1* | 12/2017 | Stein | A61B 17/7032 |

FOREIGN PATENT DOCUMENTS

| | | |
|---|---|---|
| WO | 2009015100 A2 | 1/2009 |
| WO | 2010120989 A1 | 10/2010 |

\* cited by examiner

SPINAL COLUMN IMPLANT CONNECTION DEVICE

CROSS-REFERENCE TO RELATED APPLICATIONS

The present application is a 371 of International application PCT/EP2020/071578, filed Jul. 30, 2020, which claims priority of DE 10 2019 005 374.5 filed Jul. 30, 2019, the priority of these applications is hereby claimed and the applications are incorporated herein by reference.

BACKGROUND OF THE INVENTION

The invention relates to a connecting device for connecting an end region of an already implanted first spinal column support, in which a plurality of pedicle screws are coupled at their head side to a first connecting rod by means of a coupling device in each case, comprising an already implanted or yet to be implanted spinal column support section which has a pedicle screw and which lengthens the first spinal column support, comprising a first fastening arrangement for fastening the connecting device to the first connecting rod and a coupling for the extending support section, in particular in the form of a second rod to be coupled to the pedicle screw of the extending support section or in the form of a second fastening arrangement for fastening the connecting device to such a second rod.

Such connecting devices are known and preferably used when an already existing spinal column support is no longer sufficient for its bearer, but should be lengthened so as to extend over additional vertebrae. A complete replacement of the existing spinal column support would be a greater operative burden since the existing connecting rod would have to be exposed over its entire length and released from its clamped position in order to be replaced by a longer rod, and this would be accompanied by significant restoration outlay especially in the case of frequently used spinal column supports in which loosening the fixation of the connecting rod would also cancel the coupling states of the pedicle screws and the coupling devices, which are coupled in special rotational positions in certain circumstances.

Therefore, lengthening the previously implanted system is considered. A system, known to this end, for longitudinal coupling of two connecting rods is disclosed in US 2008/234743 A1; however, it only has limited suitability for the aforementioned purposes since it assumes a thread at the coupling-side end of both rods which, as a rule, need not exist for the already implanted rod in any case. The teaching presented in WO 2010/120989 A1 manages without such a thread. In a first variant of the teaching of this document, the existing connecting rod between the two next pedicle screws on the connection side is cut off, and (only) the outermost pedicle screw is removed. A pedicle screw is then screwed into this vertebra, the coupling device of the pedicle screw has a lateral extension with a channel into which the connecting rod of the already implanted spinal column support is inserted and fastened with a screw. If, according to the teaching of WO 2010/120989 A1, the already implanted connecting rod is not to be cut off in this way, a lengthening support, as shown in FIG. 14A of this document, can be coupled on as reproduced in FIG. 6 of this application. A bypass rod 247 is placed parallel to the already existing connecting rod and connected to the already implanted connecting rod and the connecting rod of the extension via a connecting sleeve.

SUMMARY OF THE INVENTION

All of these systems have their advantages and disadvantages. The invention is based on the object of developing a connecting device of the type mentioned at the outset, which is improved in terms of a good combination of structural simplicity, simplicity in its attachment/use and low loads on the bearer.

This object is achieved by the invention by means of a connecting device of the type mentioned at the outset, which is essentially characterized by a rigid bridge of an intermediate region between the first fastening arrangement of the connecting device and the coupling, in particular between its first and second fastening arrangement or its first fastening arrangement and the second rod, said bridge laterally nestling against the coupling device of the closest pedicle screw of the already implanted spinal column support on the connection side. The connecting device according to the invention allows use without modification of the existing implanted spinal column support with simple handling while still having a satisfactory quality of the required rigid coupling. Due to the fact that it nestles against the coupling device, forces acting on the connecting device have only a small lever arm, apart from the fact that the connecting device requires less space.

In a particularly preferred embodiment, the nestling is lateral nestling on both sides. In this way, increased stability of the connecting device can be achieved with a still satisfactorily little material outlay. If the direction of extent of the spinal column support to be lengthened is a longitudinal direction, a direction of extent of the coupling device is a vertical direction and the third spatial direction is a transverse direction which forms a plane together with the longitudinal direction, the nestling of the bridge being able to be seen in the projection of said plane, a maximum dimension of the connecting device in the transverse direction is preferably less than 3 cm, preferably less than 2.7 cm, more preferably less than 2.4 cm, and in particular less than 2 cm.

Moreover, provision is preferably made for a vertical extent of the bridge to not exceed the vertical of the coupling device by more than 100%, preferably by not more than 60%, in particular by not more than 30% of the vertical dimension of the latter. In a further preferred embodiment, the vertical of the upper end of the coupling device is not higher than the vertical of the upper end of the bridge. In the latter case, the bearer does not need any space beyond the space that already exists in the vertical direction.

In a particularly preferred embodiment, the connecting device comprises a third fastening arrangement for fastening said connecting device to the first connecting rod at the free end thereof on the connection side. This further increases the stability of the connection since, as viewed in the longitudinal direction, the connecting device is fastened on both sides of the coupling device and a comparatively stable fastening is thus maintained even in the event of unintentional play due to unintentional loosening of one of the fastening arrangements.

To avoid the latter, the clamping screws to be used for the fastening arrangements can be designed to be self-locking.

In a further preferred configuration, for the purposes of positioning the connecting device in relation to the first spinal column support, the first fastening arrangement is able to be placed radially and in particular from above on the end region comprising the coupling device of the closest pedicle screw on the connection side. Positioning during use can thus be implemented in a single placement step. In this case, the regions adjoining the coupling device can form a guide during the placement.

In a further preferred embodiment in this context, the ability to be placed contains the ability of the first and/or third fastening arrangement to be clipped on by means of a (respective) resilient device. This again simplifies the attachment in use since by clipping on, a positioning that is already correctly positioned but no longer inadvertently detachable from the connecting rod is provided without tools. In addition, the correct axial positioning is also already adopted by nestling in an almost complementary shape in particular. In a preferred embodiment, the resilient device is designed in such a way that one lateral boundary of a receiving region which receives the first connecting rod and is in the form of a receiving channel is formed by the inner face of a resilient arm, and the other lateral boundary is formed on the opposite side (in the lateral/transverse direction) by a side structure of the first fastening arrangement which adopts the function of a fixed arm.

This aspect of the simple establishment of positioning is also disclosed by the invention as independently usable and worthy of protection, separately and independently of the type of design of the rigid bridge with regard to nestling.

The invention thus also relates to a connecting device for connecting an end region of an already implanted first spinal column support, in which a plurality of pedicle screws are coupled at their head side to a first connecting rod by means of a coupling device in each case, comprising an already implanted or yet to be implanted spinal column support section which has a pedicle screw and which lengthens the first spinal column support, comprising a first fastening arrangement for fastening the connecting device to the first connecting rod and a coupling for the lengthening support section, in particular in the form of a second rod to be coupled to the pedicle screw of the lengthening support section or in the form of a second fastening arrangement for fastening the connecting device to such a second rod, wherein, for the purposes of positioning the connecting device in relation to the first spinal column support, the first fastening arrangement is able to be placed radially and in particular from above on the end region comprising the coupling device of the closest pedicle screw on the connection side by means of a resilient device of the first fastening arrangement and/or a capability of clipping on the first and/or third fastening arrangement brought about by a third fastening arrangement to be fastened on the other side of the coupling device.

It is understood that the preceding and/or following further features of the connecting device can also be used jointly for this independent variant of the clip-on connecting device. The first connecting rod is preferably clamped to the first and/or third fastening arrangement by clamping means which are part of the connecting device.

In this context, provision is made for a clamping screw, in particular, to be provided, which is arranged off-centered in relation to a receiving region of the first and/or third fastening arrangement which receives the first connecting rod. The clamping screw can be screwed into a threaded bore which does not extend through to the receiving region, formed in the form of a receiving channel, for the first connecting rod. An axial direction of force application when screwing in the clamping screw is therefore no longer taken centrally with respect to the middle of the connecting rod 60 as seen in cross section and counteracts the spring action of the resilient device up to its cancellation and finally clamping of the connecting rod in the region of the fastening arrangement that receives it. For the latter, a resilient arm and a side structure of the first fastening arrangement that takes on the function of a stationary arm preferably clamp the first connecting rod in the lateral direction that runs orthogonally to the axial direction of force application.

Should the second rod for lengthening the spinal column support not yet already be a constituent part of the connecting device, the second fastening arrangement can be designed for the axial insertion of the second rod in its longitudinal direction in a preferred embodiment and in particular be formed in the form of an axial bore in a block of material. This allows the second rod to be pushed in axially, for example when the connecting device has already been clipped on. The second rod can then be fixed in the axial bore by means of locking screws. It goes without saying that lateral insertion options are also conceivable, such as U-shaped channels. The directions of extension of the rods preferably coincide, but angled arrangements are also conceivable, in particular also more complex couplings that allow polyaxial angle adjustment.

In a preferred embodiment, the maximum transverse dimension of the connecting device is less than $1/3$, preferably less than $2/7$ of its axial dimension (calculated without an optionally realized second rod) and/or less than 440%, in particular 360% of the diameter of the receiving region for the first connecting rod. A compact structure can be provided if the rigidity of the bridge is of sufficient quality. By nestling the bridge, a sleeve-like or bandage-like use can be created in a preferred embodiment of the lateral nestling on both sides, with a smaller transverse dimension of the nestling portion compared to the nestled portion at the longitudinal point of maximum transverse dimension. In the preferred implementation of the nestling by a sheath-like part, it is preferable for a wall thickness of the sheath wall in the region of the maximum transverse dimension of the connecting device to be less than 40%, preferably less than 30%, in particular less than 20% of the transverse dimension of the region enclosed by the sheath. The sheath-like part is preferably connected in one piece to the first fastening arrangement.

The invention likewise provides an extension set for lengthening an already implanted first spinal column support, comprising a connecting device according to any one of the aforementioned aspects and comprising at least one pedicle screw, a second rod (provided the latter is not optionally already a part of the connecting device) and at least one coupling device for forming a rigid connection between the pedicle screw and the second rod.

A spinal column support as a whole, having a first spinal column support with a plurality of pedicle screws, which are coupled at their head side to a first connecting rod by way of a coupling device in each case, and an extension connected by means of a connecting device according to any one of the aforementioned aspects, is also placed under protection.

The invention also protects the preparation of such a connecting device for its upcoming use in creating an extension of a first spinal column support. This can include a plurality of aspects, firstly the design of the connecting devices (provided in any case) from a materials point of view from biocompatible materials (such as titanium, stainless steel or plastics, such as biocompatible polymers, which are known to the person skilled in the art of implantology), as well as the obvious preparation through disinfection steps such as, e.g., autoclaving, the appropriate assembly matching the support rods of the first spinal column support already implanted and/or the provision of the assembled parts for the surgeon performing the implantation. With regard to the pedicle screws and their coupling devices on rods, as are known to the person skilled in the art and are addressed multiple times in this application, reference is made, for example, to techniques like in WO 2009/015100 A2 or EP 2 581 057 B1, which are incorporated by reference in this regard.

Moreover, provision is also made for providing an assortment, having at least two, in particular at least four connecting devices according to any one of the aforementioned aspects, wherein the first fastening arrangements of at least two connecting devices have a different embodiment from one another in order to be fastened to the connecting rods with different transverse dimensions, in order to be able to be placed on coupling devices of different sizes, and/or at least two connecting devices have second rods of different lengths. Such an assortment renders it possible to react flexibly to cases in which an already implanted spinal column support of known and uniform dimensions of its parts cannot be assumed, further increasing the flexibility of the use of the connecting devices.

BRIEF DESCRIPTION OF THE DRAWING

Further features, details and advantages of the invention will become apparent from the following description relating to the attached figures, in which.

DETAILED DESCRIPTION OF THE INVENTION

Figure 1A:
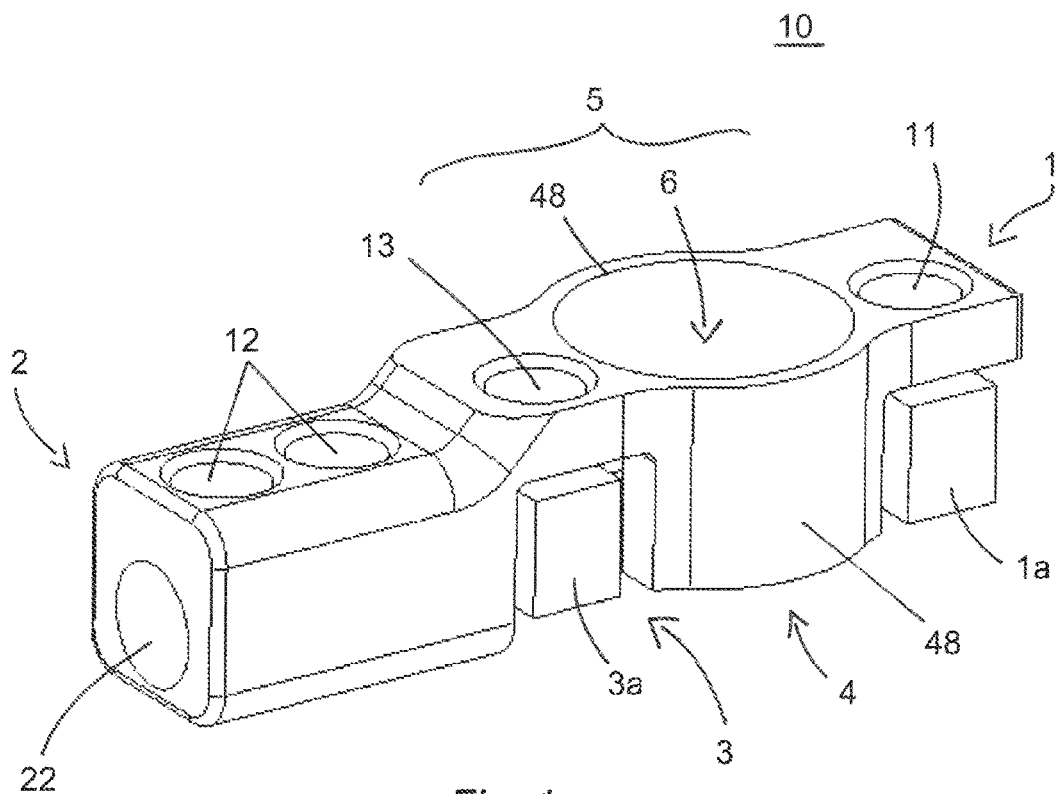
FIG. 1a is a perspective view of a connecting device of a first embodiment.

A connecting device 10 of a first embodiment is illustrated in a perspective view in FIG. 1a. A first fastening arrangement 1 with a spring arm 1a and a bore 11 provided with a thread, not shown, for screwing in a clamping screw, not shown, can be recognized far right in FIG. 1a. The first fastening arrangement 1 is used to fasten the connecting device 10 to a connecting rod 60 (FIG. 3a) of a spinal column support.

The connecting device 10 has a second fastening arrangement 2 in the left end region of FIG. 1a. This has a bore 22, which is embedded in the material of the end region and which extends in the longitudinal direction of the connecting device 10, and threaded through-bores 12 which run in the vertical direction and extend as far as the bore 22. In this way, a rod inserted into the bore 22 can be fixed by means of locking screws, not shown, which are screwed into the threaded bores 12. The second fastening arrangement 2 thus serves to fasten a rod 40 which forms part of a support which lengthens the spinal column support having the connecting rod 60, although only the rod 40 itself is shown in FIG. 3b. An intermediate region 5 between the first fastening arrangement 1 and the second fastening arrangement 2 has adjacent to the first fastening arrangement 1 a sheath-like region 4, the interior 6 of which is cylindrical in this exemplary embodiment, the cylinder axis extending in the vertical direction. As can be seen from FIG. 1a, the sheath-like region 4 is connected in one piece to the first fastening arrangement 1. In the connection use, a coupling device 80 is received in the interior 6, the coupling device coupling a pedicle screw 70 of the spinal column support to its connecting rod 60 in a fixating manner. As can be seen from FIG. 1a, the first fastening arrangement 1 and the second fastening arrangement 2 are connected to one another in one piece via the intermediate region 5.

Between the sheath-like region 4 and the second fastening arrangement 2 there is also a third fastening arrangement 3 with a spring arm 3a and threaded bore 13, which in this exemplary embodiment is structurally identical to the first fastening arrangement 1 and is explained below with reference to FIG. 2. The third fastening arrangement 3, like the fastening arrangement 1, serves to fix the connecting device to the connecting rod 60 of an already implanted spinal column support, but on the side of the coupling device 80 facing away from the fastening arrangement 1, at the free end of the connecting rod 60. The first and third fastening arrangements 1, 3 thus in a sandwich-like manner surround the coupling device of the spinal column support to be lengthened, and the sheath-like region 4 or its lateral walls 48 nestle against the coupling device 80. As can be seen from FIG. 1a, the first fastening arrangement 1 and the third fastening arrangement 3 are connected to one another in one piece via the sheath-like region 4.

Figure 2A:
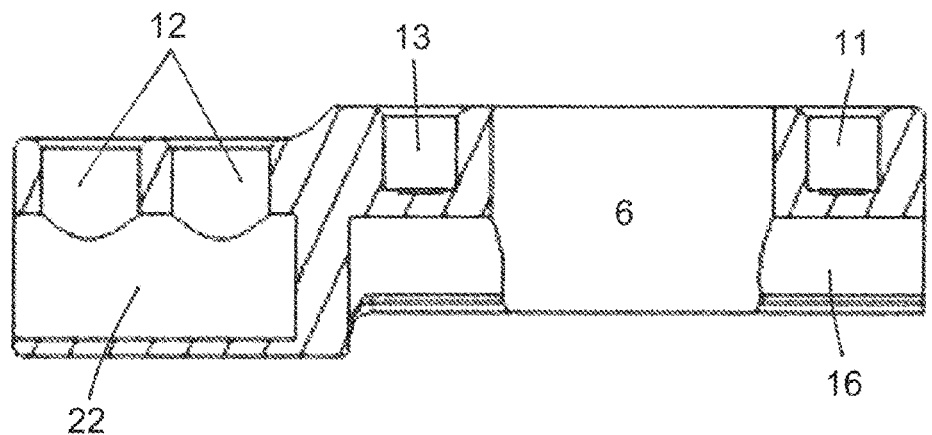

As can be seen in FIG. 2a, a receiving channel 16 for the connecting rod 60 runs axially centrally and almost coaxially to the bore 22 in this exemplary embodiment. In the region of the first and third fastening arrangement, the mouth opening of the channel 16 in the unloaded state of the spring arms 1a, 3a is slightly narrower than the diameter of the channel 16. Thus, with elastic yielding of their resilient arms 1a, 3a the fastening arrangements 1, 3 can be clipped onto the connecting rod 60, while the sheath-like region 4 is slipped over the coupling device 80 during this clipping-on movement.

Figure 1B:
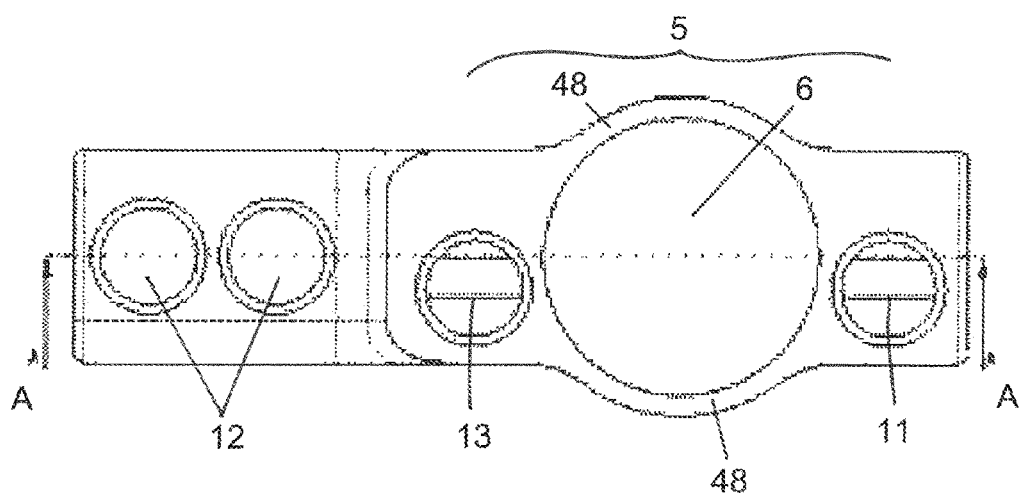
FIG. 1b is a plan view of the connecting device of FIG. 1a, FIG. 2a comprises a sectional view taken along the line A-A from FIG. 1a, FIG. 2b comprises a sectional view taken along the line B-B in FIG. 1b.
Figure 2B:
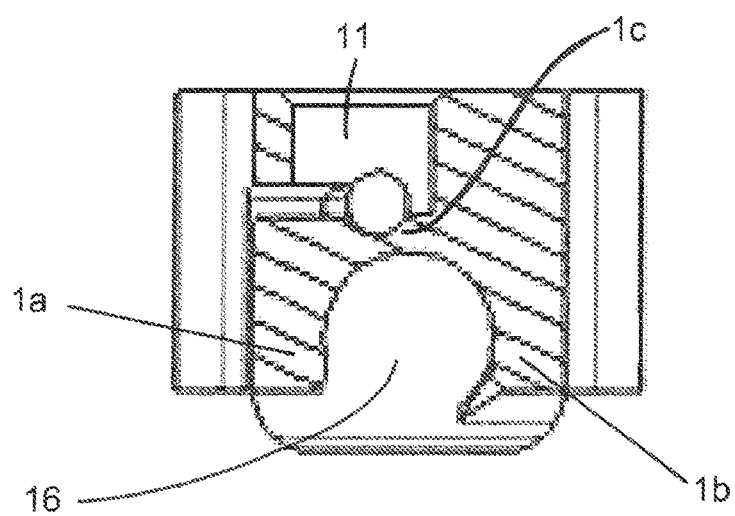

The threaded bores 11 and 13 do not extend as far as the channel 16 (FIG. 2). Additionally, as can be seen in FIG. 1b and FIG. 2b, these are arranged off-centered in relation to the central axis of the connecting device 10 and displaced in the direction of the resilient arms 1a, 3a, and so when the clamping screws are screwed in, the resilient effect of the spring arms 1a, 3a is initially canceled and taking the connecting device 10 off the spinal column support (rod 60) again is blocked in this state. With further tightening or securing of the clamping screws, the connecting device 10 is rigidly and firmly connected to the connecting rod 60 of the already implanted spinal column support. The rod 40 of the lengthening section of this spinal column support is thus also rigidly and firmly connected via the second fastening arrangement 2 to the spinal column support to be lengthened. As can be seen from FIG. 2b, the thread for the bore 11 and the opposing lateral boundaries of the channel 16 are connected to one another in one piece.

In this exemplary embodiment, the function of clipping-on the fastening arrangement 1 is realized by virtue of, as viewed in cross section to the channel 16, the boundary thereof being formed on one side by the inner face of the resilient arm 1a, on the opposite side by a side structure of the fastening arrangement 1 adopting the function of the fixing arm 1b, and the two arms 1a and 1b being connected to one another only by a material bridge 1c of small thickness. The material and dimensions of the material bridge 1c are, however, matched to one another in such a way that the resilient arm 1a is prevented from breaking off in the event of accidental, unintentional application of force. As can be seen from FIG. 2b, the lateral boundaries 1a, 1b of the channel lie opposite one another with respect to a transverse direction or lateral direction, which runs orthogonally to the threaded bore 11. As already explained above, the threaded bore 11 is not arranged centrally with respect to the lateral boundaries 1a, 1b, but is displaced off-center in the transverse direction towards the spring arm 1a.

Figure 3A:
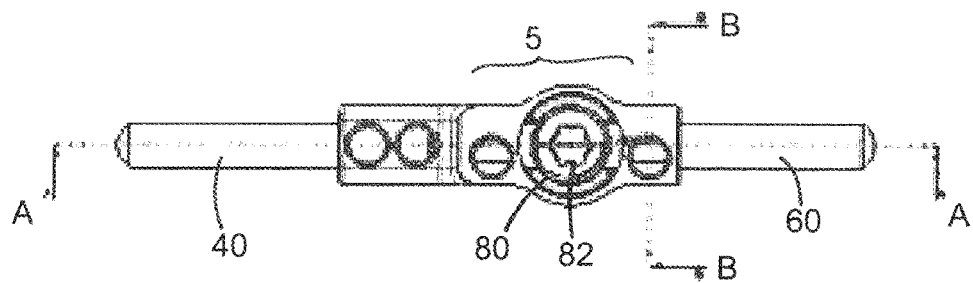
FIG. 3a shows a top view of the connecting device from FIG. 1a in its connecting use, FIG. 3b comprises a sectional view along the line A-A from FIG. 3a, FIG. 3c comprises a sectional view along the line B-B in FIG. 3a, FIG. 4 shows a second embodiment of a connecting device, FIGS. 5a, 5b, 5c correspond to FIGS. 3a, 3b and 3c for this second embodiment.
Figure 3B:
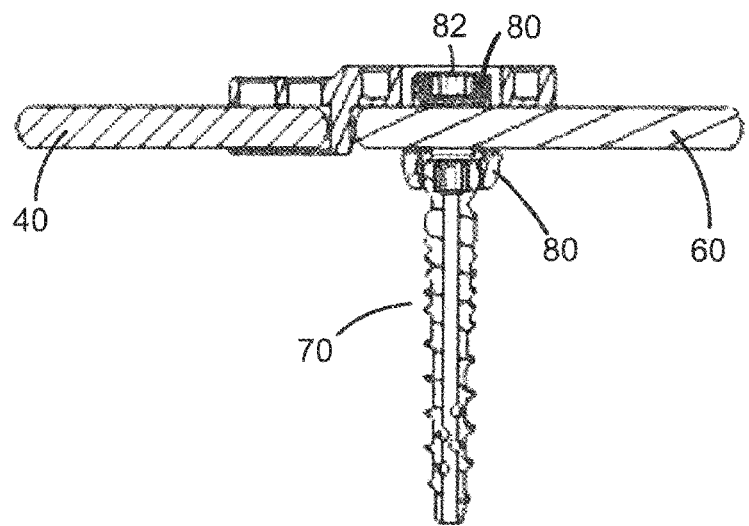
Figure 3C:
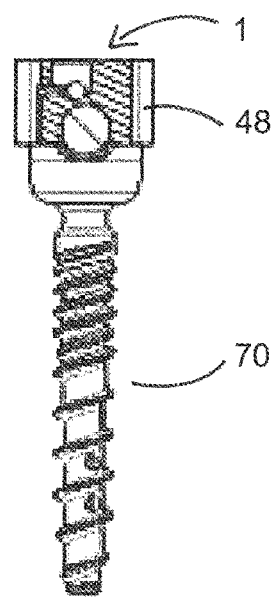

In addition to the illustrated sectional representations, constituent parts recognizable in projection are also imaged in the figure representations of FIG. 3, for instance the pedicle screw 70 in FIG. 3c or the side regions 48 of the sheath-like region 4, so as to be able to recognize the relative position of these parts/objects. It can be clearly seen from FIG. 3a in particular that the side of the connecting device 10 that is coupled to the connecting rod 60 wraps like a sleeve or bandage around the end region of the already implanted spinal column support that has not only the connecting rod 60 but also the coupling device 80. In this exemplary embodiment, the maximum transverse dimension of the connecting device 10, formed here by the transverse spacing between the two side walls 48 of the sheath-shaped region 4, thus is only about 2.5 times the diameter of the connecting rod 60 or the channel 16 designed to accommodate it.

The connecting device 10 can simply be clipped onto this end region without requiring a manipulation of the end region on the rod 60 and/or the coupling device 80, and without requiring loosening of the locking screw 82 of the coupling device 80. The latter can be designed according to the techniques used over the years, which are described for example in WO 2009/015100 A2 or EP 2 581 057 B1, with, for example, a tulip, a saddle received in the tulip in which the head of the pedicle screw 70 is received, and the screw 82 which exerts clamping pressure on the saddle via the connecting rod 60 for the fixed coupling of the screw 70, in particular designed as a polyaxial screw, in the desired angular position in relation to the connecting rod 60. Similar systems can then also be used for the lengthening spinal column support section with the rod 40.

When viewed in the vertical direction, as shown in FIG. 3b, the upper section of the coupling device 80 can be received entirely within the interior 6 of the sheath-like region 4. In this way, a comparatively flat surface side of the connecting device can be formed in the deployed state.

It is apparent to a person skilled in the art that various alternative structural designs are conceivable for this embodiment, for example the axes for the rods 40, 60 need not be collinear, not even parallel, if angled connections are required. The second fastening arrangement 2 could also be designed differently, for example similar to the first fastening arrangement or with a lateral insertion channel instead of the blind hole 22. The sleeve-like nestling could also be achieved by lateral clipping onto the connecting rod 60; for this purpose, the sheath-like region 4 would have to be modified to suit a lateral attachment. In the case of a correspondingly rigid configuration, one of the side arms 48 of the sheath-like region 4 can also suffice. The downwardly protruding flange-like end portions of the side walls 48 could, for example, be shorter or have incisions, or the structure of the sheath-like region can be replaced by a ring structure corresponding to its upper region. In the case of very short protruding free ends of the connecting rod 60, variants are also considered in which the third fastening arrangement is displaced to the side of the first fastening arrangement or the first fastening arrangement alone ensures sufficient coupling to the connecting rod 60.

Figure 4:
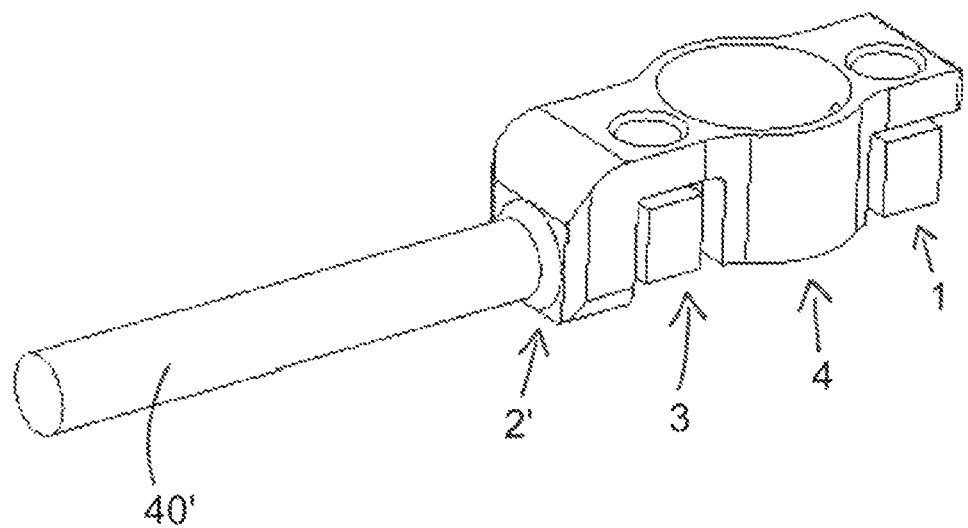
Figure 5A:
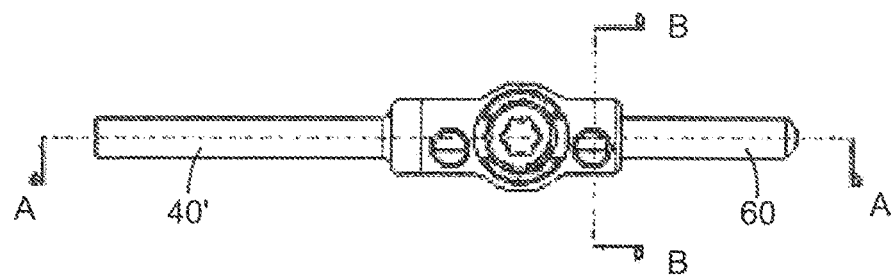
Figure 5B:
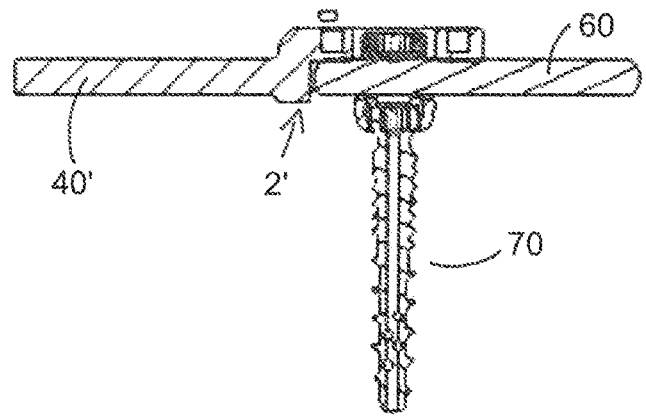
Figure 5C:
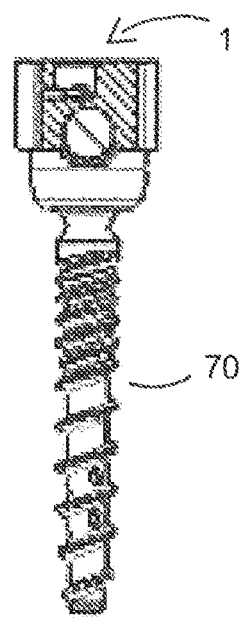
Figure 6:
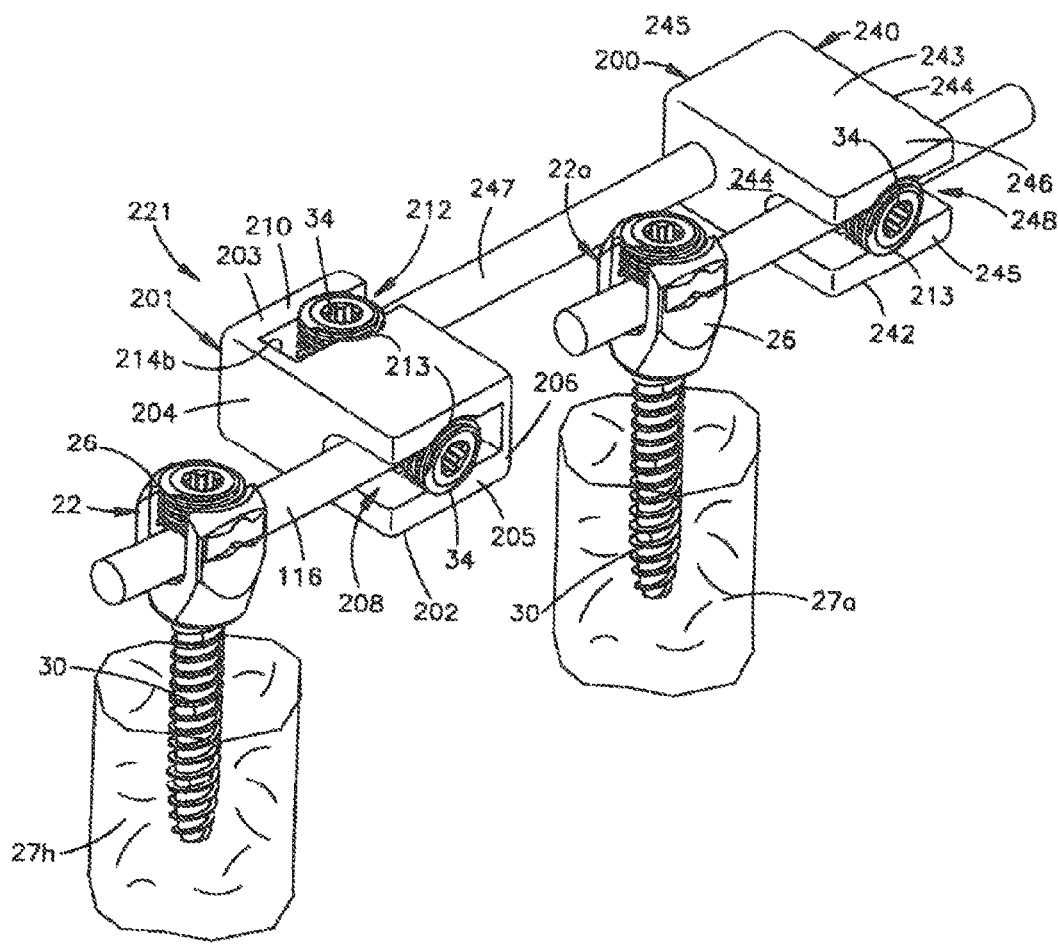
FIG. 6 shows a connecting device known from the prior art.

Additionally, the rod of the lengthening section can already be a firmly coupled constituent part of the connecting device. Such an embodiment is shown in FIG. 4 in a schematic representation. What can be seen is that in the connecting device 10' shown there, the rod 40' acting to lengthen the rod 60 is already connected in one piece, for instance via a flange 2' of the connecting device 10' adjacent to the third fastening arrangement 3. As can be seen from FIG. 4, the flange 2' and the first fastening arrangement 1 are connected to one another in one piece via the intermediate region 5. In this way, a plurality of connecting devices 10' with rods 40' of different lengths can also be provided, depending on the length dimension of the extension required. The rest of the design of the connecting device 10' can correspond to that of the connecting device 10 from FIG. 1a, in this respect the same reference signs are also used to denote equivalent parts, and the representations in FIGS. 5a, 5b and 5c correspond, functionally and constructively in this exemplary embodiment, to the representation of figure group 3 of the first embodiment, precisely apart from the already provided rod 40'. It is understood that mixed forms can also be used, for example the connection between rod 40' and flange 2' could be formed not in one piece and a rod 40" could be screwed into a flange 2" instead.

In terms of material, the constituent parts of the connecting device are made of a biocompatible material, such as stainless steel, titanium or biocompatible polymers, as they are known as such to the person skilled in the art.

Preparing the connecting device for use can comprise a disinfection step and/or an autoclaving step, and also the appropriate provision of not only the connecting device, but also the entire lengthening spinal column support with a connecting rod 40 (40', 40") of appropriate length and pedicle screws/coupling devices similar to the pedicle screw 70 and coupling device 80 shown in FIGS. 3 and 5, for the specific designs of which conventional structures are available, such as those presented in the documents referred to above.

The invention is therefore not restricted to the embodiments described in the examples illustrated. Rather, the individual features of the above description and the following claims can be essential individually and/or in combination for the implementation of the invention in its various embodiments.

The invention claimed is:

1. A connecting device for connecting an end region of an already implanted first spinal column support, in which a plurality of pedicle screws are respectively coupled at a head side to a first connecting rod by a respective coupling device in each case, comprising an already implanted or yet to be implanted spinal column support section which has a pedicle screw and which lengthens the first spinal column support, the connecting device comprising:
    a first fastening arrangement for fastening the connecting device to the first connecting rod;
    a coupling for a lengthening support section;

a rigid bridge of an intermediate region between the first fastening arrangement and the coupling, said bridge laterally nestling against the coupling device of a closest of the pedicle screws of the already implanted first spinal column support on the connection side, wherein, for purposes of positioning the connecting device in relation to the first spinal column support, the first fastening arrangement is configured to be placeable radially and from above on an end region comprising the coupling device of the closest pedicle screw on the connection side;

clamping means for clamping the first connecting rod to the first fastening arrangement;

a resilient device that has a resilient arm with an inner face that forms one lateral boundary of a receiving region that receives the first connecting rod and is formed as a receiving channel, wherein another lateral boundary is formed on an opposite side of the receiving channel by a side structure of the first fastening arrangement, which acts as a fixed arm; and, a clamping screw arranged off-center and writable into a threaded bore that does not extend through to the receiving channel so that an axial direction of force application by the clamping screw is not central with respect to a middle of the connecting rod as seen in cross-section and counteracts spring action of the resilient device to a point of cancellation of the spring action and subsequent clamping of the connecting rod in the receiving channel.

2. The connecting device according to claim 1, wherein the coupling for the lengthening support section is a second rod coupleable to the pedicle screw of the lengthening support section or is a second fastening arrangement for fastening the connecting device to such a second rod.

3. The connecting device according to claim 1, wherein the lateral nestling formed by the bridge further comprises an opposing lateral nestling formed on the opposite side of the bridge.

4. The connecting device according to claim 2, wherein the bridge has a vertical extent that does not exceed a height of the coupling device by more than 100% of a vertical dimension of the coupling device.

5. The connecting device according to claim 4, wherein the vertical extent of the bridge that does not exceed the height of the coupling device by more than 60% of the vertical dimension of the coupling device.

6. The connecting device according to claim 5, wherein the vertical extent of the bridge that does not exceed the height of the coupling device by more than 30% of the vertical dimension of the coupling device.

7. The connecting device according to claim 2, further comprising a third fastening arrangement for fastening said connecting device to the first connecting rod at a free end thereof on the connection side.

8. The connecting device according to claim 7, wherein the connecting device is configured to be top-loadable.

9. The connecting device according to claim 8, further including a further resilient device arranged to clip the third fastening arrangement when the connecting device is top-loaded.

10. The connecting device according to claim 9, wherein the clamping means includes an additional clamping screw arranged off-centered in relation to a receiving region of the third fastening arrangement that receives the first connecting rod.

11. The connecting device according to claim 2, wherein the second fastening arrangement includes a block of material having an axial bore configured for axial insertion of the second rod in a longitudinal direction of the second rod.

12. The connecting device according to claim 2, configured for substantially collinear relative positioning of the first connecting rod and the second rod.

13. The connecting device according to claim 9, having an axial dimension and a maximum transverse dimension that is less than $\frac{1}{3}$, preferably less than $\frac{2}{7}$ of the axial dimension, and/or less than 440%, in particular 360% of a diameter of the receiving region for the first connecting rod.

14. The connecting device according to claim 13, wherein the maximum transverse dimension is less than $\frac{2}{7}$ of the axial dimension.

15. The connecting device according to claim 13, wherein the maximum transverse dimension is less than 360% of the diameter of the receiving region for the first connecting rod.

16. An extension set for lengthening an already implanted first spinal column support, comprising: a connecting device according to claim 1; at least one pedicle screw; a second rod, optionally already as part of the connecting device; and at least one coupling device for forming a rigid connection between the pedicle screw and the second rod.

17. The extension set according to claim 16, made of a biocompatible material.

18. A spinal column support, comprising: a first spinal column support with a plurality of pedicle screws, which are each coupled at a head side to a first connecting rod by a respective coupling device; and an extension connected by a connecting device according to claim 1.

19. An assortment, comprising: at least two connecting devices according to claim 1, wherein the first fastening arrangements of the two connecting devices are embodied differently from one another in order to be fastened to connecting rods with different transverse dimensions so as to be placeable on coupling devices of different sizes, and/or the at least two connecting devices have second rods of different lengths.

* * * * *